United States Patent [19]

Galbraith

[11] Patent Number: 4,601,576
[45] Date of Patent: Jul. 22, 1986

[54] LIGHT COLLECTOR FOR OPTICAL CONTAMINANT AND FLAW DETECTOR

[75] Inventor: Lee K. Galbraith, Mountain View, Calif.

[73] Assignee: Tencor Instruments, Mountain View, Calif.

[21] Appl. No.: 559,909

[22] Filed: Dec. 9, 1983

[51] Int. Cl.[4] ............................................. G01N 21/00
[52] U.S. Cl. .................................... 356/237; 356/430; 250/563; 250/572
[58] Field of Search ............... 356/237, 238, 239, 230, 356/232, 388, 390, 392, 430, 431, 446; 250/562, 563, 572

[56] References Cited

U.S. PATENT DOCUMENTS

| | | | |
|---|---|---|---|
| 3,663,824 | 5/1972 | Blaisdell et al. | 250/219 R |
| 3,712,979 | 1/1973 | Padgitt | 356/237 |
| 4,321,630 | 3/1982 | Kramer | 358/294 |
| 4,360,275 | 11/1982 | Louderback | 356/446 |
| 4,378,159 | 3/1983 | Galbraith | 356/237 |
| 4,412,746 | 11/1983 | Yokouchi | 356/446 |

Primary Examiner—John E. Kittle
Attorney, Agent, or Firm—Thomas Schneck

[57] ABSTRACT

A two-stage light collector, including a first stage which admits a scanning beam and a second stage which is optically connected to the first stage and has a light detector therein. The first stage has a shape which re-images diffusely scattered radiation from a target on which the radiation impinges. The first stage directs light toward an entrance aperture in the second stage which indirectly reflects light toward the detector associated with the second stage.

13 Claims, 5 Drawing Figures

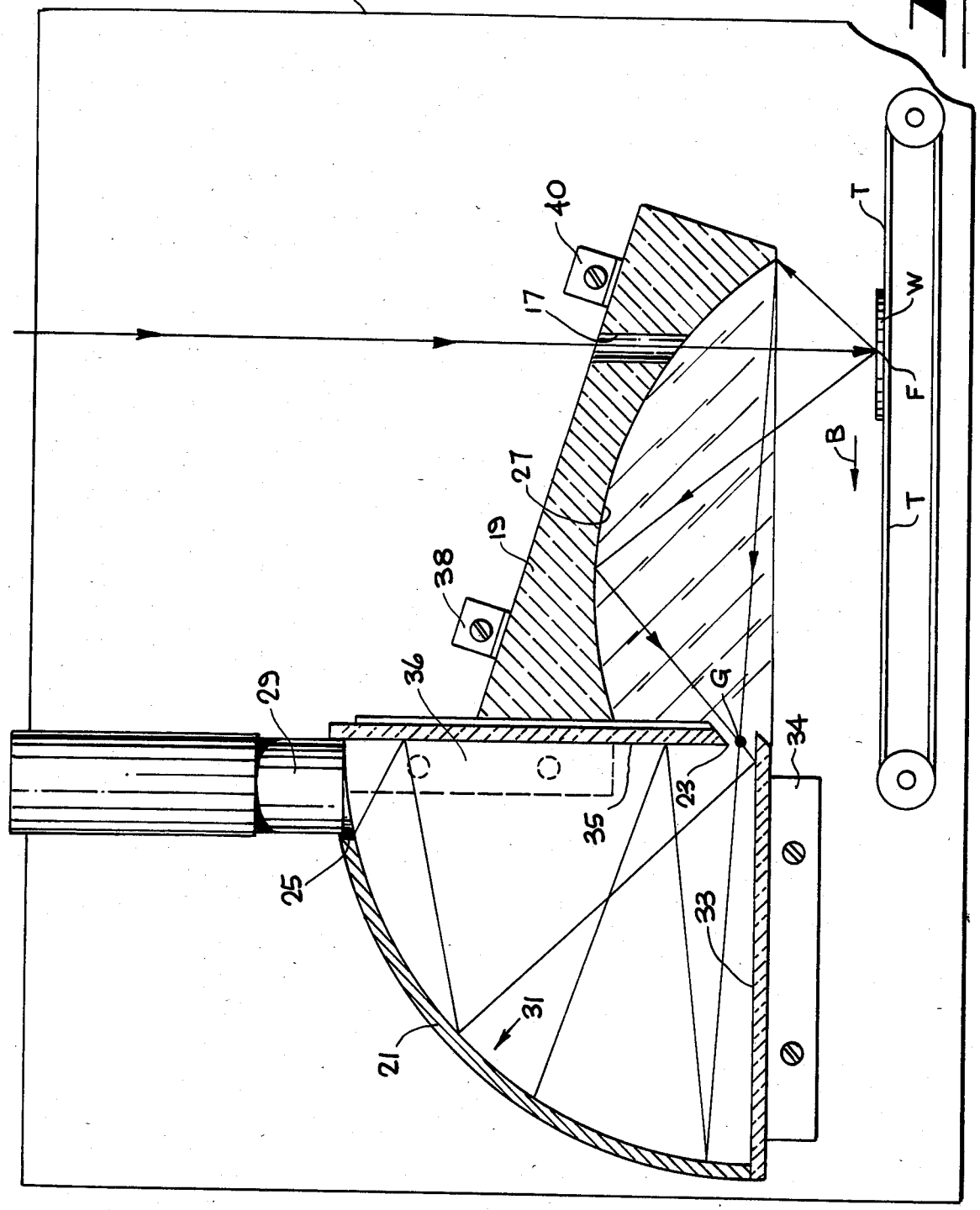

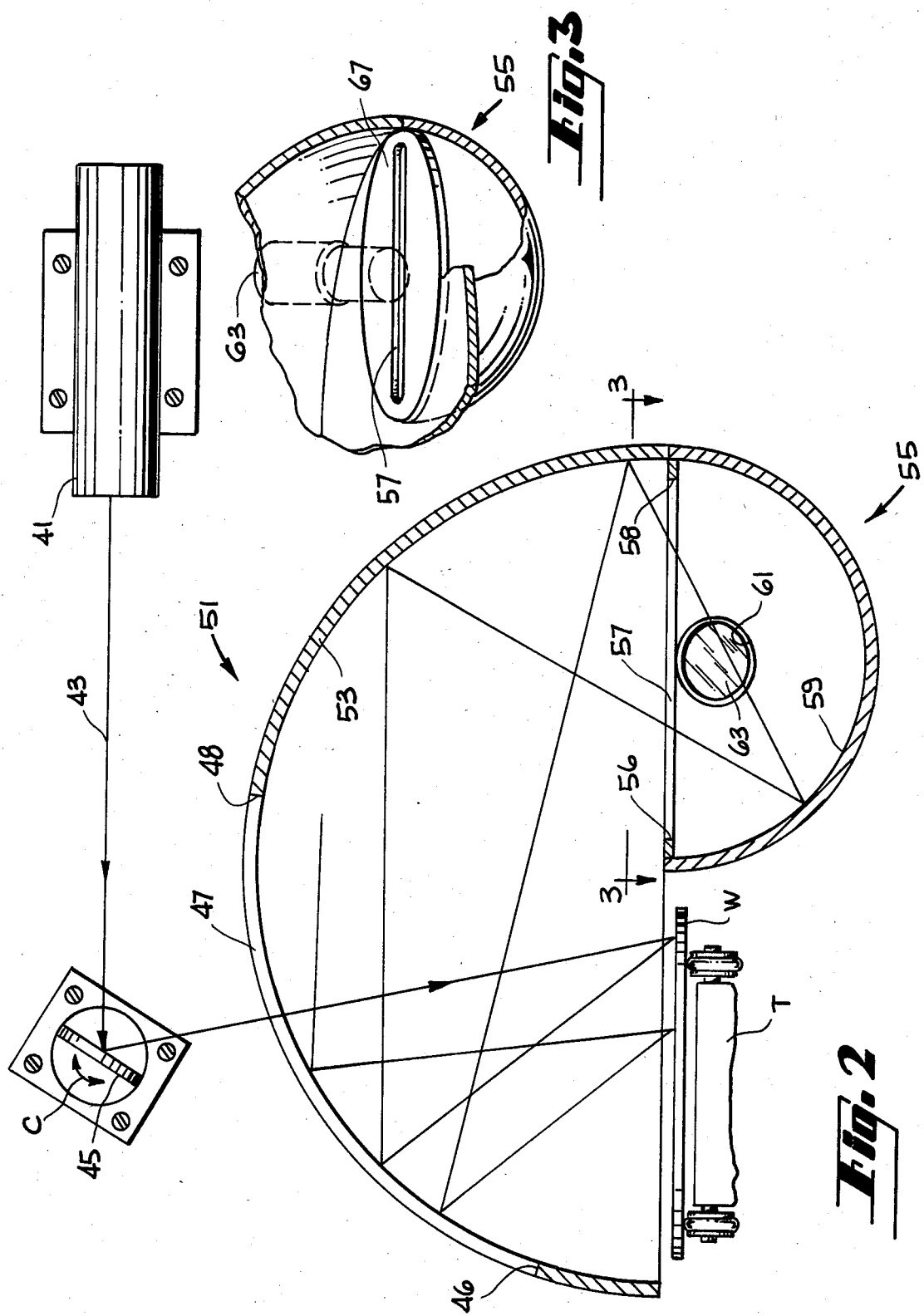

LIGHT COLLECTOR FOR OPTICAL CONTAMINANT AND FLAW DETECTOR

TECHNICAL FIELD

The invention relates to optical flaw and contaminant detectors and more particularly to a scanning laser contaminant detector for reflective surfaces, such as silicon wafers.

BACKGROUND ART

In U.S. Pat. No. 4,378,159, owned by the assignee of this application, L. K. Galbraith describes a scanning laser contaminant and defect detector which uses a light collector for increasing the sensitivity of the detector. In other words, the effective aperture of the detector is modified by use of a light collector to gather diffusely reflected light.

In the prior device, the collector is a quadrant of a diffusely reflective spherical shell cradled between V-shaped, specularly reflective side walls. The shell has beam entrance and exit ports, as well as a detector port where a light detector resided. The collector is placed in proximity to a test surface to be inspected. Light scattered from the test surface is directed to the interior of the reflective shell surface, then to the reflective side walls and ultimately to the detector.

One of the problems of prior laser scanners was unwanted scattered light; i.e., scattered from other than the target surface, reaching the detector. For example, dirt particles on the scanning mirror can scatter light. This light behaves as if it originates at a new source having properties different from the main beam. The unwanted light has a high probability of collection at the detector once it enters the light collector. The unwanted light is considered to be optical "noise," lowering the overall signal-to-noise ratio of the instrument.

An object of the invention was to achieve increased sensitivity in a scanning contaminant and defect detector by limiting the effects of light scattered from other than the target surface.

DISCLOSURE OF INVENTION

The above object has been achieved with a scanning contaminant and defect detector wherein a two-stage light collector is used. A first stage admits the beam, directs light to the test surface, collects the light and selectively feeds it to a second stage which directs the light to a detector over an extended optical path. Each stage is a separate light collector.

In one embodiment the first stage comprises a cylindrical mirror having an elliptical cross section. Since an elliptical cylinder has two line foci, one focus may be placed on a test surface, while the other focus may be placed at the entrance port of the second stage. By taking advantage of the optical symmetry of these foci, light may be selectively transferred from one collector to another. Light is admitted to the first stage and directed towards a test surface. A large fraction of the light scattered from the test object along the first line focus will be delivered to the second stage at the second line focus, which is the conjugate of the first.

The second stage has a diffusely reflective spherical shell cradled between V-shaped, specularly reflective side walls, resembling the light collector shown in U.S. Pat. No. 4,378,159. However, the entrance slit in the second stage, at the junction of V-shaped side walls, coincides with second focus of the first stage. Light entering the second stage is collected at the detector.

A benefit of using two distinct collector stages is that light scattered from other than the target surface may enter the first stage light collector, but will have a low probability of reaching the focus of the first stage and being introduced into the second stage. This improves the signal-to-noise ratio of scanning contaminant and defect detectors.

BRIEF DESCRIPTION OF THE DRAWINGS

FIG. 1 is a side view of an improved light collector in accord with the present invention.

FIG. 2 is a side view of an alternate embodiment of an improved light collector in accord with the present invention.

FIG. 3 is a side cutaway view of a detail of the apparatus shown in FIG. 2, taken along lines 3—3.

BEST MODE FOR CARRYING OUT THE INVENTION

Figure 1A:
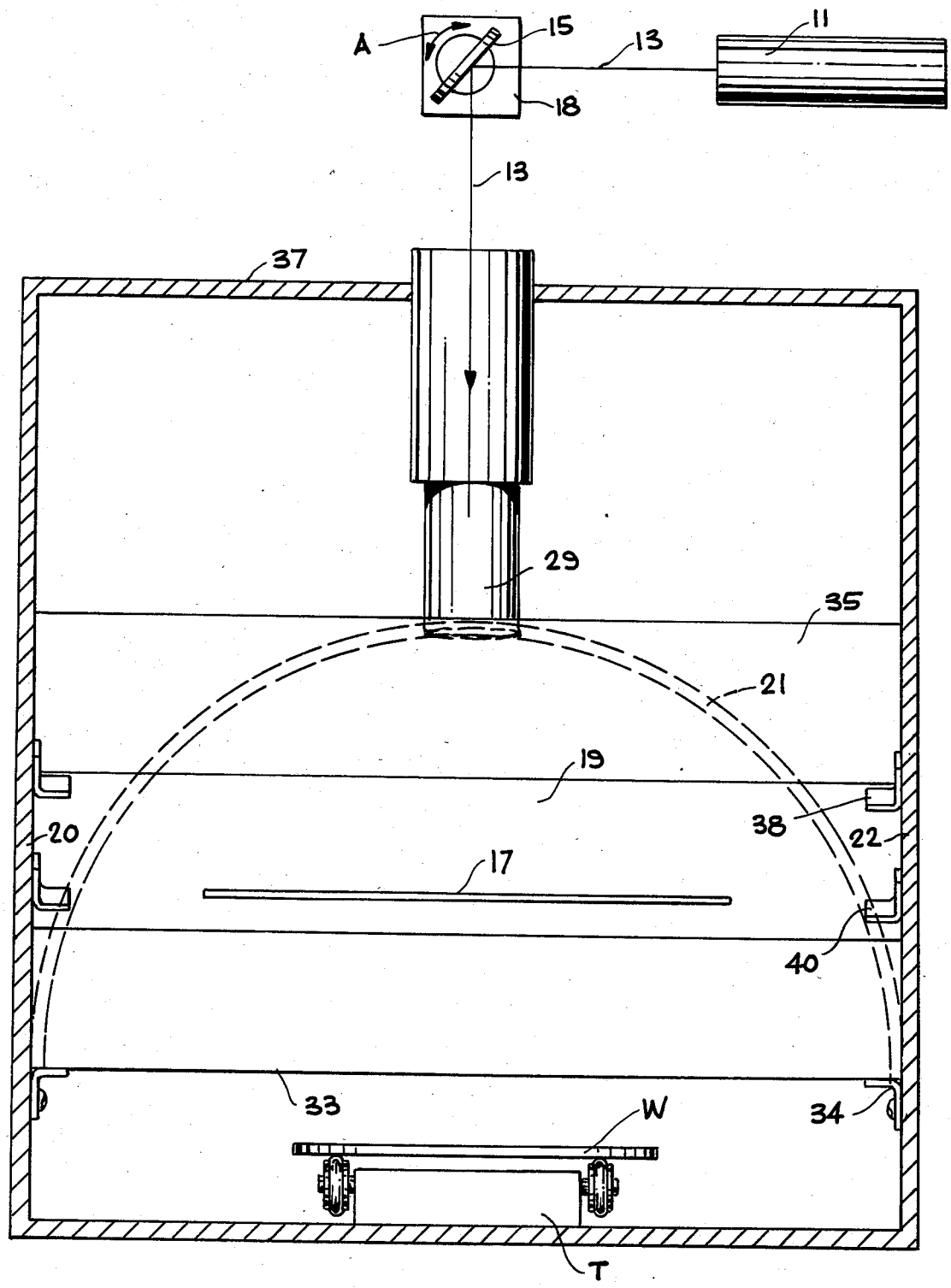
FIG. 1a is a front elevational view of the light collector shown in FIG. 1.

With reference to FIGS. 1 and 1a, a low power laser 11 is shown directing a beam 13 toward a rotating or oscillating mirror 15. The laser 11 can be a helium-neon general purpose laser having an output power of a few milliwatts. A higher power laser may be preferable for greater detection capability. In some instances blue light, e.g. from a helium-cadmium laser is preferred for detection of smaller defects than with a helium-neon laser. Focussing optics, not shown, may be interposed between the laser and the mirror. From the scanning center of mirror 15, the beam is directed to an entrance aperture 17 within the first light collector 19. Mirror 15 is mounted in a holder 18 and is driven by a galvanometer coil so that the mirror can make rapid oscillations, in the directions indicated by arrows A, sweeping the beam over a narrow range of angles so that the beam can scan the width of a test object, such as wafer W. The beam entrance aperture 17 should be wide enough to accommodate beam motion across the entire width of the wafer W.

Wafer W is mounted on a conveyor or wafer transport T. As the mirror 15 rocks back and forth in the directions indicated by the arrows A and the beam is swept across the surface wafer W, linear motion of the wafer on the wafer transport T in the direction of arrow B allows a complete area scan of the wafer surface. The scan of the wafer by the beam corresponds to raster scanning of a CRT display device. In fact, the mirror speed may be synchronized with the CRT beam writing speed so that CRT scans correspond to mirror scans of the test surface.

The purpose of the first light collector 19 is to collect light and selectively direct it into a second light collector 21. Previously, in the prior art, a single light collector would have both a beam entrance aperture and a beam exit aperture with a detector. This did not provide any discrimination against unwanted light being collected. Now, however, a second light collector 21 is provided with a narrow beam entrance aperture 23 which receives light primarily from a focal line F on the surface of wafer W. A detector 29 is placed at a beam exit aperture 25 which is not directly in the path of rays entering beam entrance aperture 17. The first light collector 19 must have an internally specularly reflective surface 27 which will deliver light to the entrance aperture 23. Light collector 19 is cylindrical across the width of its holder, i.e., between side walls 20 and 22 and has a cross sectional surface 27 which is elliptical. The light collector is supported between opposed side walls 20 and 22 and a cross sectional shape of the collector between the walls is preferably identical, from edge to edge. An ellipse has the property of having two focal points. Correspondingly, an elliptical cyclinder has two focal lines. The elliptical cylinder is laid out so that a first focal line, F, of the ellipse will lie on the wafer W. All of the light collected from this focal line will be delivered to a second focal line G which is made to coincide with the center of the entrance aperture 23 of the second light collector. The gap at line G, forming the entrance aperture to the second collector, is carefully controlled in width to about 3 millimeters. This is done to eliminate light from the second collector which did not originate at the first focal line F. It is important that the target be located such that focal line F falls right on the target surface so that light which is in the vicinity of the first focal line will be delivered to the vicinity of the second focal line within a close tolerance. The second entrance aperture 23 is made large enough to accommodate light from the vicinity of the first focal line F, as well as from the entirety of wafer W. However, the second entrance aperture 23 must be limited to prevent entry of unwanted light, and escape of light from the second collector.

The interior surfaces of side walls 20 and 22 should be flat mirrors parallel to each other and perpendicular to the axis of the elliptical cylinder. These insure that light rays scattered obliquely along the wafer scan line and propagating toward the side walls 20 or 22 will nevertheless enter the second collector after reflection from the side walls and the elliptical cylinder.

The construction of the second light collector 21 is quite similar to the light collector described in the aforementioned U.S. Pat. No. 4,378,159. Collector 21 has an internal surface 31 which is a diffusely reflective surface of a sector of a spherical shell. High reflectivity is desired and this is achieved by white paint or the like coating the surface. The surface 31 is cradled between two specularly reflective mirrors 33 and 35 forming side walls. The purpose of the walls is to provide support for surface 31, as well as to re-direct light back onto the surface 31 until it reaches detector 29. A gap, G, exists at the junction of the mirror side walls 33 and 35 forming a beam entrance aperture 23 into the second light collector 21. Mirrors 33 and 35 may be supported by means of brackets 34 and 36 respectively, the latter bracket indicated by dashed lines. Mirror surface 27 may be supported by brackets 38 and 40.

Detector 29 is positioned at a location where it will not be the recipient of directly entrant light rays. Rather, the light rays reaching detector 29 usually have been reflected between surface 31 and either or both of the side walls 33 and 35 a number of times. The detector is a photomultiplier tube which converts impinging optical radiation to a corresponding electrical signal. This signal may be displayed on a CRT, or recorded, or both. The electrical signal may also be converted to a digital signal and manipulated by digital techniques.

The entire apparatus is preferably housed in a light tight container 37 in which the various components are mounted. The container has opposed lateral walls 20 and 22 to which the various components are connected by means of brackets, such as brackets 34, 36, 38 and 40. Additionally, a bracket supports source 11. Mirrors 33 and 35, as well as surface 27 are all supported between opposed lateral walls of the housing.

FIG. 2 shows the second embodiment of a two-stage light collector including a low power laser 41 directing a beam 43 toward a galvanometer-driven mirror 45. The beam is directed to a beam entrance aperture 47 which is an elongated slit having ends 46 and 48 in a first stage light collector 51 having a specularly reflective hemispherical surface 53 for collecting light.

Beam 43 is directed through the beam entrance aperture 47 to a specularly reflecting target object, such as wafer W. The wafer is mounted on a wafer transport T to move in and out of the plane of the paper. The width of slit 47 is just wide enough to accommodate the scanning beam moving in the directions indicated by arrows C. Light which is scattered from the surface of wafer W thence goes to the interior wall of surface 53 which is specularly reflective. Specularly reflected light from the wafer escapes through entrance slot 47. Most of the scattered light is captured within the first stage 51. Light diffusely reflected and scattered from the scanning line on the surface of wafer W is directed by specular reflection to a symmetrically located line on the other side of the hemisphere. This new line corresponds to the entrance aperture or slit 57 in the second collector 55. While a hemispherical shape has been mentioned for the configuration of surface 53, other shapes, such as ellipsoidal could also work. Shapes must be figures or revolution about an axis in the plane of the paper and coinciding with the plane of the wafer and the plane of the second collector entrance slot 65. A second stage light collector 55, smaller in size than the first stage, is connected to the first stage for receiving light through a slit 57 between end regions 56 and 58. This collector has an internally diffusely reflective surface 59 with a beam exit aperture 61, located at approximately right angles to the beam entrance direction, so that an entering beam cannot directly enter a detector 63, mounted near the exit aperture. The surface 59 is preferably spherical. The first and second light collector stages should be mounted such that one receives light from the other.

FIG. 3 illustrates the configuration of a slit 57 in the upper wall 67 of the second light collector 55, the upper wall 67 being a plane mirror. Slit 57 is centered at the corresponding line image of the scanning line made by beam 43 across the surface of wafer W. The symmetric location of the slit 57 relative to the scanning line insures that a fair amount of light reflected from the wafer will be collected in the second stage, through the slit 57. The spherical interior surface of the second stage is diffusely reflective such that light, once entering the second stage, will reflect until it is either lost back through the slit 57 or captured by detector 63.

It will be seen that the embodiment of FIG. 3 is similar in operation to the embodiment described with reference to FIG. 1. Beam 43 scans the test surface W through slit 47. Since the scanning line across the test surface corresponds symmetrically with slit 57, light which is specularly reflected by the walls of the first light collector 51 passes through the slit 57. Once inside the diffusely internally reflecting second light collector 55, light is eventually collected at the detector 63. By synchronizing motion of the test surface W on the transport T with the scanning beam, a raster pattern may be developed on a CRT, showing contrast variations wherever particles are encountered on the test surface. In such an instance, the amount of scattering from the test surface increases dramatically and a signal in the detector is almost simultaneously produced. Such signals allow a point-for-point inspection of a test surface.

Figure 4:
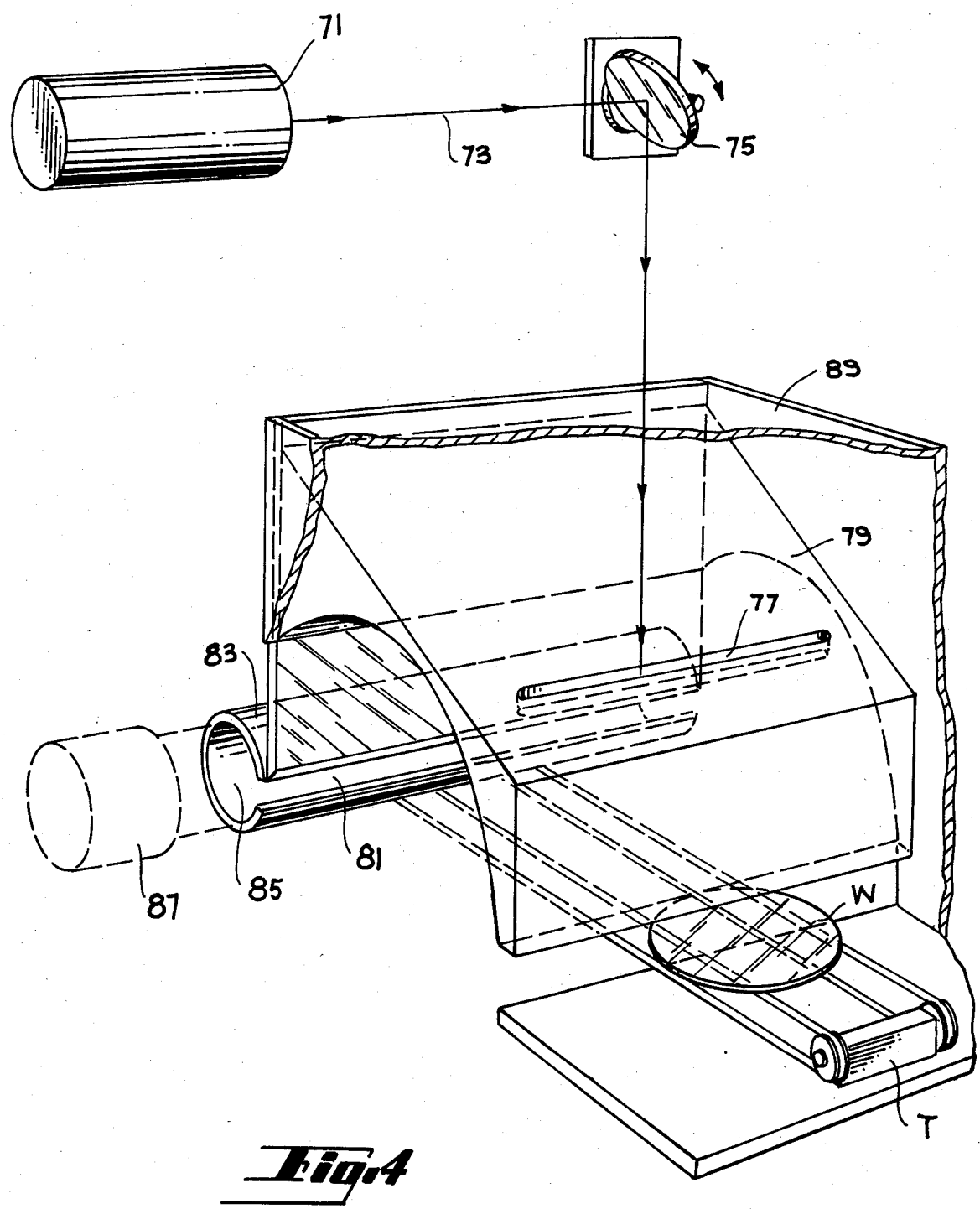
FIG. 4 is a perspective view of another alternate embodiment of a light collector in accord with the present invention.

With reference to FIG. 4, laser 71 is seen directing a beam 73 toward the galvanometer mirror 75. This mirror directs light into a slot 77 in a first light collector 79. Light collector 79 is identical to the first light collector 19 in FIG. 1. This light collector is cylindrical in shape, but has an elliptical cross section. Such a light collector has two focal lines, one of which is on the wafer W being transported by the wafer transport T, the other focal line being at the entrance aperture 81 of a pipe 83 having a diffusely reflective interior wall 85. Light is reflected within the pipe, with light being detected by a photomultiplier tube 87 at one end of the pipe. The entire apparatus can be made light-tight by providing a housing 89 enclosing the first light collector. If the second light collector is similarly enclosed, ambient light is restricted from the apparatus.

In the embodiments set forth herein, light was directed onto a reflective test surface. It will be realized that the apparatus of the present invention may be utilized for defect detection in non-reflective surfaces, for example in scanning for holes in fabric or fiber webs. In this instance, the first light collector may have light directed through a fabric from below the test surface and into the collector region, thereby obviating the need for a slot in the collector.

In the pesent invention, light is collected in a first light collector and selectively transmitted to a second, adjacent light collector where it is measured. By locating the second collector at a conjugate focal location of the first light collector, selective transmission of light is carried out. This improves the signal-to-noise ratio in an optical scanning and inspection device.

I claim:

1. A two-stage light collector for detecting contaminants and defects on a test surface comprising,
   a light source capable of generating a narrow beam,
   a support holding a test surface with a number of light scattering contaminants and defects,
   scanning means for sweeping the beam in a path across the test surface,
   a first light collector having an entrance aperture for admitting the beam, and having a beam exit aperture, said first light collector directing light scattered from said test surface to said beam exit aperture and
   a second light collector having an entrance aperture in optical communication with the beam exit aperture of the first light collector and having a detector port distal from light entering said entrance aperture of said second light collector with light detection means mounted therein for detecting changes in light scattering from said test surface, light scattered from locations other than from said test surface having a low probability of entering said second light collector and being detected.

2. The light collector of claim 1 wherein said support comprises a wafer transport means for moving wafers across the beam path.

3. The light collector of claim 1 wherein said first light collector comprises an internally reflecting shell.

4. The light collector of claim 1 wherein said second light collector comprises an internally reflecting shell.

5. The light collector of claim 3 wherein said internally reflecting shell of said first light collector has an elliptical cross section.

6. A two-stage light collector for detecting contaminants and defects on a test surface comprising,
   a light source capable of generating a narrow beam,
   a support holding a reflective test surface,
   a sector of an internally diffusely reflecting spherical shell cradled between specularly reflective, flat converging side walls having a linear gap along a line of convergence,
   a sector of an internally reflecting elliptical shell having first and second foci, including a first focal line disposed within said linear gap on said line of convergence and a second focal line disposed on the surface of the test object being scanned by the beam, said elliptical shell having a beam entrance aperture for admitting a scanning beam,
   optical means for directing said narrow beam toward said beam entrance aperture and scanning means for sweeping the beam in a path across the test surface, light scattered from said test surface being directed by said elliptical shell from said first focal line to said second focal line into said spherical shell, and
   light detection means in communication with scattered light within said spherical shell for detecting increases and decreases in scattered light from said test surface within the spherical shell, light scattered from locations other than from said test surface having a low probability of being detected.

7. The light collector of claim 6 wherein said elliptical shell has its reflective surface facing said test surface, said elliptical shell having a linear slot therein accommodating said beam.

8. The light collector of claim 6 wherein said spherical shell has a detector port mounting said light detection means, said detector port distal from light entering said beam entrance aperture.

9. The light collector of claim 6 wherein said spherical shell and said elliptical shell have flat lateral walls supported by a housing.

10. The light collector of claim 6 wherein at least one beam blocking member is disposed in said elliptical shell for blocking light rays from entering said spherical shell at undesired angles.

11. The light collector of claim 1 wherein said first light collector comprises an internally reflecting hemispherical shell and said second light collector comprises an internally diffusely reflecting hemispherical shell having a diameter which is smaller than the diameter of said first light collector, said shell of said second light collector having an entrance aperture diametrically opposed to said beam path across said test surface.

12. The light collector of claim 4 wherein said second light collector comprises an internally reflecting cylindrical shell.

13. A two-stage light collector for detecting contaminants and defects on a test surface comprising,
   a light source capable of generating a narrow beam,
   a support holding a reflective test surface,
   a first internally reflecting hemispherical shell having a beam entrance aperture for admitting a scanning beam,
   a second internally diffusely reflecting hemispherical shell with a plane mirror upper wall having a slit in the wall, optical means for directing said narrow beam toward said entrance aperture and scanning means for sweeping the beam in a path across said test surface, light scattered from said test surface being directed by said first shell from said beam path to said slit into said second shell, said slit being diametrically opposite said beam path, light detection means in communication with scattered light within said second shell for detecting increases and decreases in light scattered from said test surface within said second shell, light scattered from locations other than said beam path on said test surface having a low probability of entering said second shell and being detected.

\* \* \* \* \*